US009119531B2

(12) United States Patent
Surti et al.

(10) Patent No.: US 9,119,531 B2
(45) Date of Patent: Sep. 1, 2015

(54) VISUALIZATION CATHETER PERISCOPE

(71) Applicant: Cook Medical Technologies LLC, Bloomington, IN (US)

(72) Inventors: Vihar C. Surti, Winston-Salem, NC (US); John Crowder Sigmon, Jr., Greensboro, NC (US); Tyler Evans McLawhorn, Winston-Salem, NC (US); Michelle D. Martinez, Winston-Salem, NC (US); Richard W. Ducharme, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 395 days.

(21) Appl. No.: 13/659,001

(22) Filed: Oct. 24, 2012

(65) Prior Publication Data

US 2013/0110003 A1 May 2, 2013

Related U.S. Application Data

(60) Provisional application No. 61/552,095, filed on Oct. 27, 2011.

(51) Int. Cl.
*A61B 1/06* (2006.01)
*A61B 1/00* (2006.01)
*A61B 1/018* (2006.01)
*A61B 1/07* (2006.01)

(52) U.S. Cl.
CPC ........... *A61B 1/00101* (2013.01); *A61B 1/0008* (2013.01); *A61B 1/00165* (2013.01); *A61B 1/018* (2013.01); *A61B 1/07* (2013.01)

(58) Field of Classification Search
USPC .......... 600/121–125, 129, 136, 175–177, 200
See application file for complete search history.

(56) References Cited

U.S. PATENT DOCUMENTS

| | | | | |
|---|---|---|---|---|
| 4,911,148 A | * | 3/1990 | Sosnowski et al. | 600/136 |
| 4,919,112 A | * | 4/1990 | Siegmund | 600/136 |
| 4,947,245 A | * | 8/1990 | Ogawa et al. | 348/66 |
| 5,005,943 A | * | 4/1991 | Fort | 385/117 |
| 5,188,093 A | * | 2/1993 | Lafferty et al. | 600/109 |
| 5,190,028 A | | 3/1993 | Lafferty et al. | |
| 5,199,417 A | * | 4/1993 | Muller et al. | 600/128 |
| 5,329,936 A | * | 7/1994 | Lafferty et al. | 600/109 |
| 5,573,493 A | * | 11/1996 | Sauer et al. | 600/121 |
| 5,682,199 A | * | 10/1997 | Lankford | 348/72 |
| 5,733,242 A | * | 3/1998 | Rayburn et al. | 600/120 |
| 5,846,183 A | * | 12/1998 | Chilcoat | 600/136 |
| 5,879,289 A | * | 3/1999 | Yarush et al. | 600/179 |
| 6,004,263 A | * | 12/1999 | Nakaichi et al. | 600/176 |
| 6,095,970 A | * | 8/2000 | Hidaka et al. | 600/110 |
| 6,322,498 B1 | * | 11/2001 | Gravenstein et al. | 600/120 |

(Continued)

OTHER PUBLICATIONS

Notification of Transmittal of the International Search Report and the Written Opinion of the International Searching Authority, or the Declaration, dated Feb. 13, 2013, for corresponding application No. PCT/US2012/061544, 5p.

*Primary Examiner* — Matthew J Kasztejna
(74) *Attorney, Agent, or Firm* — Brinks Gilson & Lione

(57) ABSTRACT

The exemplary embodiments illustrated provide the discovery of methods and apparatuses for periscope devices that couple to a viewing end of a visualization catheter or endoscope to extend the viewing range and accessory range of the endoscope or visualization catheter so as to provide for greater viewing and reach into multiple areas of the anatomy.

18 Claims, 4 Drawing Sheets

(56) References Cited

U.S. PATENT DOCUMENTS

| | | | |
|---|---|---|---|
| 6,419,627 B1 * | 7/2002 | Ben Nun | 600/125 |
| 6,494,826 B1 * | 12/2002 | Chatenever et al. | 600/112 |
| 6,875,169 B2 * | 4/2005 | Berci et al. | 600/112 |
| 6,929,600 B2 * | 8/2005 | Hill | 600/120 |
| 7,212,737 B2 * | 5/2007 | Dehmel et al. | 396/17 |
| 8,517,922 B2 * | 8/2013 | Koitabashi et al. | 600/136 |
| 8,523,764 B2 * | 9/2013 | Hatcher et al. | 600/136 |
| 8,702,594 B2 * | 4/2014 | Edidin et al. | 600/136 |
| 8,887,730 B2 * | 11/2014 | Wood et al. | 128/207.14 |
| 2007/0088198 A1 * | 4/2007 | Koitabashi et al. | 600/136 |
| 2007/0219412 A1 | 9/2007 | DiGiovanni et al. | |
| 2011/0098528 A1 | 4/2011 | Lewinsky | |

\* cited by examiner

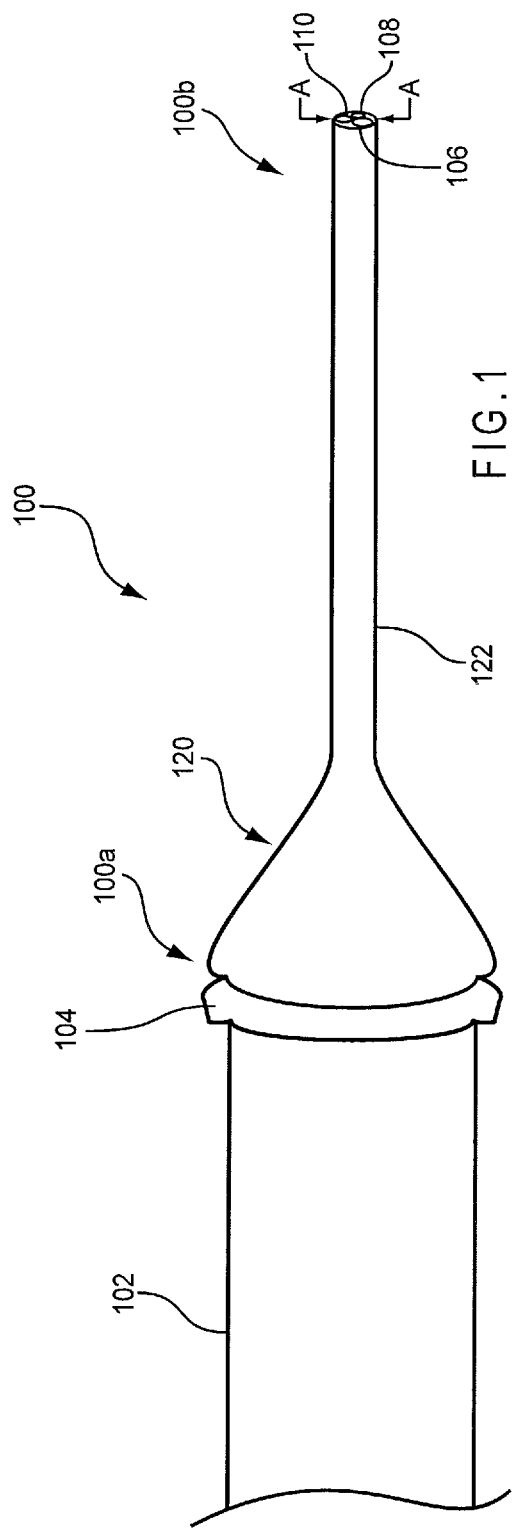
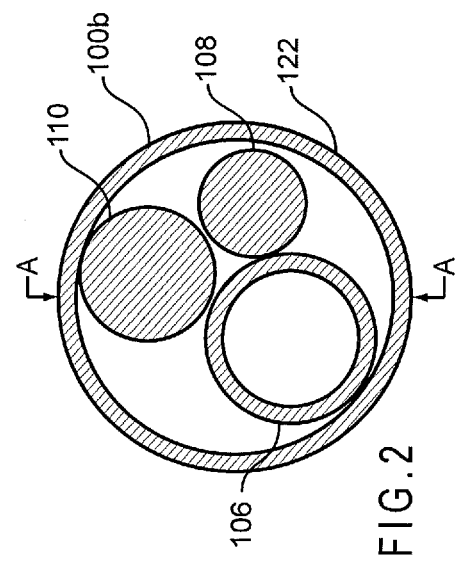

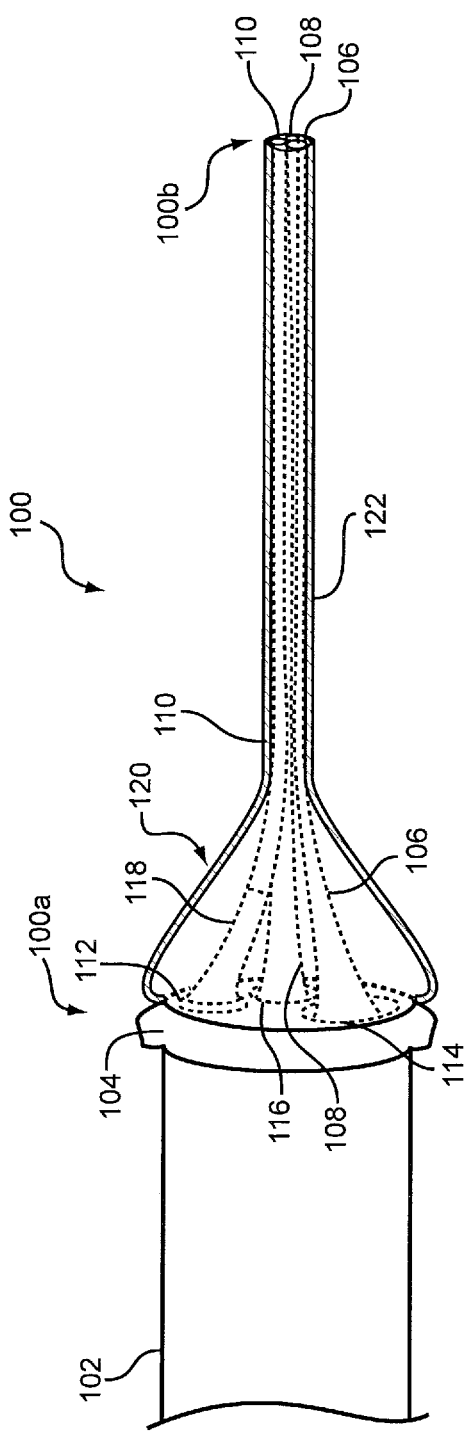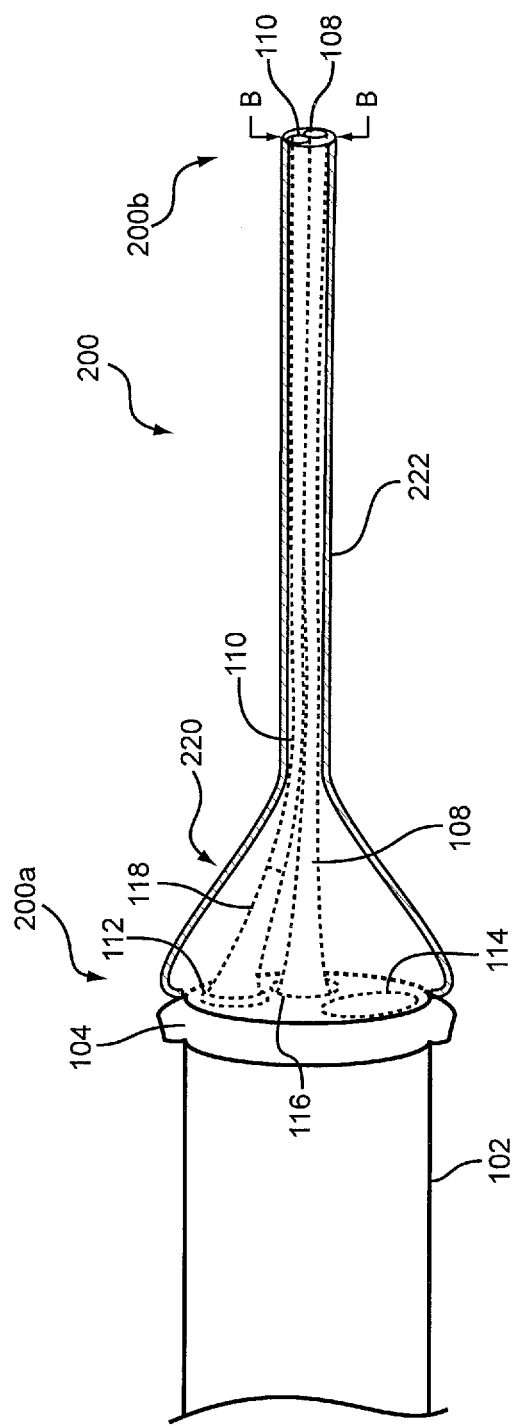

VISUALIZATION CATHETER PERISCOPE

TECHNICAL FIELD

The present invention relates to medical devices and more specifically, visualization catheters.

BACKGROUND

Endoscopes are routinely used to provide direct visualization to medical personnel while performing medical procedures. To enable medical personnel to reach smaller portions of the anatomy, medical personnel often use a mother-baby scope technique. Baby scopes are either fiber optic ocular lens scopes or electronic, and they typically have an outer diameter of 3.5 mm. Using a mother-baby scope technique, a baby scope is directed through a working channel of an endoscope, such as a forward-viewing gastroscope or a side-view duodenoscope, and thereafter directed to the targeted anatomy.

For example, endoscopic retrograde cholangiopancreatography (ERCP) is a commonly used endoscopic procedure to both diagnose and treat ailments of both the pancreatic and bile duct systems. Often, a side-viewing endoscope (duodenoscope) is advanced to the duodenum and in line with the ampulla of Vater (papilla) to facilitate diagnostic and therapeutic catheter-based procedures. A method to gain direct visualization of the bile and pancreatic ducts is use of a mother scope/baby scope system where the mother scope is a duodenoscope and the baby scope is a choledochoscope that is passed through the accessory channel of the duodenoscope.

The mother-baby scope approach presents numerous problems and issues. For example, the technique is difficult to use for a number of reasons, including but not limited to, requiring two sets of operators, two sets of equipment, and accordingly, additional resources. Moreover, due to the outer diameter size of the mother scope and the baby scope, the possible anatomical areas able to be visualized and treated by such an approach are limited.

Alternatively, rather than use a mother-baby scope approach, a slim scope may be considered. A slim scope has an outer diameter of approximately 5-7 mm, and therefore, it cannot be passed through the accessory channel of a duodenoscope. Instead, an overtube is used to provide structure for the slim scope to facilitate cannulation into the bile duct.

The slim-scope approach presents numerous problems and issues. The technique is difficult to use for a number of reasons. For example, the overtubes that are used in conjunction with the slim scope cannot bend where the slim scope exits at the distal end of the overtube, nor can the distal end of the overtubes be held in a fixed position. As a result, the slim scope often falls out of the bile duct or other targeted anatomy because of its extra weight compared to a lighter baby scope.

BRIEF SUMMARY

In a first aspect, a periscope is provided, including a cylindrical body including a proximal portion and a distal portion; wherein the cylindrical body is tapered along at least a portion of the cylindrical body; a first fiber optic cable disposed within the cylindrical body and extending from the proximal portion of the cylindrical body to the distal portion of the cylindrical body; a lens stack in communication with the cylindrical body; and a second fiber optic cable in communication with the lens stack, wherein the second fiber optic cable is disposed within the cylindrical body and extends to the distal portion of the cylindrical body.

In a second aspect, a periscope is provided, including a cylindrical body including a proximal portion and a distal portion; wherein the cylindrical body is tapered along at least a portion of the cylindrical body; a first fiber optic cable disposed within the cylindrical body and extending from the proximal portion of the cylindrical body to the distal portion of the cylindrical body; a lens stack disposed at the proximal portion of the cylindrical body; a second fiber optic cable in communication with the lens stack, wherein the second fiber optic cable is disposed within the cylindrical body and extends to the distal portion of the cylindrical body; and an accessory channel including a lumen disposed within the cylindrical body and extending from the proximal portion of the cylindrical body through the distal portion of the cylindrical body; wherein the proximal portion of the cylindrical body further includes an attachment means configured for attachment to a viewing end of an endoscope such that the first fiber optic cable is coaxial with a light of the endoscope, the lens stack is coaxial with a camera of the endoscope, and the accessory channel is coaxial with a working channel of the endoscope.

In a third aspect, a method of using a periscope device is provided, including directing a wire-guide to a target site; connecting a periscope to a viewing end of an endoscope; wherein the periscope is configured to extend the view of the endoscope; back-feeding the wire-guide through the periscope and a working channel of the endoscope; and guiding the periscope to the target site.

BRIEF DESCRIPTION OF THE SEVERAL VIEWS OF THE DRAWINGS

The embodiments will be further described in connection with the attached drawing figures. It is intended that the drawings included as a part of this specification be illustrative of the exemplary embodiments and should in no way be considered as a limitation on the scope of the invention. Indeed, the present disclosure specifically contemplates other embodiments not illustrated but intended to be included in the claims. Moreover, it is understood that the figures are not necessarily drawn to scale.

FIG. 1 illustrates a perspective view of a periscope coupled to the viewing end of an endoscope;

FIG. 2 illustrates a front-view at the line A-A of the periscope illustrated in FIG. 1;

FIG. 3 illustrates a cross-sectional perspective view of the periscope illustrated in FIG. 1;

FIG. 4 illustrates a cross-sectional perspective view of an alternate embodiment of a periscope coupled to the viewing end of an endoscope;

DETAILED DESCRIPTION OF PRESENTLY PREFERRED EMBODIMENTS

Figure 5:
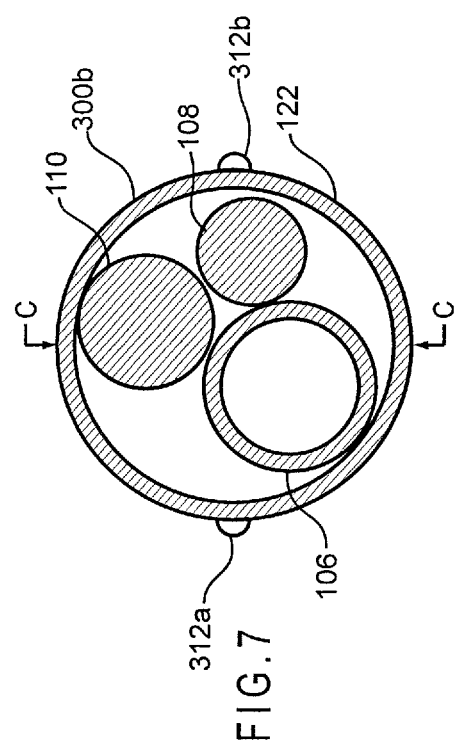
FIG. 5 illustrates a front-view at the line B-B of the periscope illustrated in FIG. 4.

The exemplary embodiments illustrated provide the discovery of methods and apparatuses of periscopes that couple to the viewing end of a visualization catheter or endoscope, such as, for example, a forward or side-viewing endoscope, including but not limited a gastroscope or duodenoscope. The periscopes illustrated and equivalents thereto extend the viewing range and accessory reach to targeted anatomy areas that were previously unviewable, unreachable, difficult to view, and/or difficult to access using a visualization catheter or endoscope. Embodiments of apparatuses, methods, and equivalents thereto provide many benefits, including but not limited to, better direct visual feedback of a targeted anatomy located at a distance away from the viewing end of the endoscope. Another benefit includes, but is not limited to, a greater ability to enter into small areas of the anatomy not otherwise reachable or viewable at the viewing end of a typical endoscope.

Diseases and conditions contemplated for treatment include, but are not limited to, those involving the gastrointestinal region, esophageal region, duodenum region, biliary region, colonic region, as well as any other bodily region or field benefiting from direct visualization of or access to a target site for treatment or diagnosis.

The present invention is not limited to those embodiments illustrated herein, but rather, the disclosure includes all equivalents including those of different shapes, sizes, and configurations, including but not limited to, other types of visualization catheters, endoscopes, and component parts. The devices and methods may be used in any field benefiting from a visualization catheter, endoscopes, or parts used in conjunction with visualization catheters and endoscopes. Additionally, the devices and methods are not limited to being used with human beings; others are contemplated, including but not limited to, animals.

Unless otherwise defined, all technical and scientific terms used herein have the same meaning as commonly understood by one of ordinary skill in the art. In case of conflict, the present document, including definitions, will control. Preferred methods and materials are illustrated below, although apparatuses, methods, and materials similar or equivalent to those illustrated herein may be used in practice or testing. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of" and "consisting essentially of," the embodiments or elements presented herein, whether explicitly set forth or not.

The term "proximal," as used herein, refers to a direction that is generally towards a physician during a medical procedure.

The term "distal," as used herein, refers to a direction that is generally towards a target site within a patient's anatomy during a medical procedure.

A more detailed description of the embodiments will now be given with reference to FIGS. 1-8. Throughout the disclosure, like reference numerals and letters refer to like elements. The present disclosure is not limited to the embodiments illustrated; to the contrary, the present disclosure specifically contemplates other embodiments not illustrated but intended to be included in the claims.

FIG. 1 illustrates a perspective view of periscope 100 coupled to the viewing end of endoscope 102, FIG. 2 illustrates a front-view of periscope 100 at the line A-A illustrated in FIG. 1, and FIG. 3 illustrates a cross-sectional perspective view of periscope 100. Referring to FIGS. 1-3, periscope 100 includes proximal portion 100a and distal portion 100b. Periscope 100 has an overall length of about 35 cm, although other dimensions are contemplated depending upon the targeted anatomy. Proximal portion 100a of periscope 100 is configured for attachment to the viewing portion of an endoscope or visualization catheter by way of an attachment means, such as elastic friction fit 104. Other means for attachment are contemplated including, but not limited to, an adhesive, a clamp, a snap-fit connection, a threaded connection, a magnetic connection, a vacuum connection, or combination thereof.

Periscope 100 is configured to extend the existing imaging and light sources beyond that of a typical endoscope or visualization catheter, such as endoscope 102. Unlike a mother-baby scope approach, periscope 100 does not require separate image processing or multiple users to operate. Unlike a slim-scope approach, periscope 100 is sufficiently rigid such that it prevents premature removal or falling out from the targeted anatomy, such as a bile duct.

Still referring to FIGS. 1-3, disposed within periscope 100 is light fiber 108 that is concentric with light source 116 of endoscope 102. Accordingly, light fiber 108 of periscope 100 extends the reach of light from endoscope 102. Light fiber 108 is preferably about 35 cm long, although other dimensions are contemplated.

Also disposed within periscope 100 is lens stack 118. Lens stack 118 is disposed at proximal portion 100a of periscope and between camera lens 112 of endoscope 102 and camera optical fiber 110 of periscope 100. Camera optical fiber 110 is preferably a single fiber optic cable that is about 15-20 cm long and is concentric with camera lens 112 of endoscope 102. There between the proximal end of camera optical fiber 110 and camera lens 112 of endoscope 102 is lens stack 118 that provides for focusing of the image targeted at distal end 100b of periscope 100. Accordingly, an image is viewed at distal end 100b of periscope 100 with camera optical fiber 110 and brought into focus with lens stack 118 and viewed by camera lens 112 of endoscope 102. Alternatively, one or more additional lens stacks may be placed at distal end 100b of periscope 100 or elsewhere, including external to periscope 100, to further enhance or alter the focus of the target site. Camera optical fiber 110, lens stack 118, and light fiber 108 are coupled to the distal end of endoscope 102 to prevent misalignment during use.

Also disposed within periscope 100 is accessory channel 106, a lumen extending through proximal portion 100a and distal portion 100b of periscope. Accessory channel 106 is coaxial with working channel 114 of endoscope 102. As illustrated herein, accessory channel 106 is bound by a thickness of material in the interior and the wall surface of periscope 100 on the exterior. Alternatively, accessory channel 106 may be bound by camera optical fiber 110 and light fiber 108 so as to further reduce the overall diameter of periscope 100 by reducing a wall thickness. Additionally, it is contemplated that one or more protrusions could extend from periscope 100 and into working channel 114 of endoscope 102 to prevent unintended rotation of periscope 100.

Because light source 116 of endoscope 102 and the targeted image site are spaced a set distance apart at its distal end, light fiber 108 and camera optical fiber 110 may have a transition length along body 122, such as tapered portion 120. Tapered portion 120 may extend any distance between and including proximal portion 100a and distal portion 100b of periscope 100 such that light fiber 108, camera optical fiber 110, and accessory channel 106 are brought extremely close together to reduce the overall outer diameter of periscope 100. Accordingly, accessory channel 106 is brought tangent to light fiber 108 and camera optical fiber 110, such that the diameter of accessory channel 106 is reduced from a proximal diameter of about 3.7 mm (11 French) to a distal diameter of about 2.0 mm. Such a configuration provides numerous benefits, including but not limited to, providing periscope 100 with an outer distal diameter of about 5 mm or less while permitting for the passage of accessory devices and instruments there through. For example, a biopsy device may be introduced through accessory channel 106 to take tissue samples; use of other therapeutic or diagnostic instruments or devices having a size of 5 Fr. or smaller are contemplated; use of other therapeutic or diagnostic instruments or devices having other sizes are contemplated depending upon the accessory channel size of the periscope.

Body 122 of periscope 100 may be made from numerous materials such that it is configured with sufficient flexibility yet maintains enough column strength to traverse the targeted anatomy. As illustrated in FIGS. 1-3, body 122 is a substantially cylindrical extruded tube. Alternatively, body 122 may be constructed efficiently by common materials and methods of construction, including but not limited to, micro-molding, machining, and using numerous materials. Body 122 may further comprise one or more rigid portions and one or more portions more flexible than the one or more rigid portions. The one or more flexible portions may be configured to aid in steering. For example, the one or more flexible portions may comprise one or more vertebrae modules. Alternatively, the one or more flexible portions may comprise ribs. Alternatively, the one or more flexible portions may comprise grooves or cuts made into the same material as that of the one or more rigid portions. Alternatively, body 122 may be configured with a first rigid portion for accepting an endoscope, a second portion configured for flexibility and steering ease, and a third portion configured to be more rigid. Alternatively, body 122 may be configured with a soft portion and a rigid portion, wherein the interiors of each section change throughout the device to aid with steering or to achieve other benefits.

FIG. 4 illustrates a cross-sectional perspective view of periscope 200 coupled to the viewing end of endoscope 102, and FIG. 5 illustrates a front-view of periscope 200 at the line B-B illustrated in FIG. 4. Referring to FIGS. 4-5, periscope 200 includes proximal portion 200a and distal portion 200b. Periscope 200 has an overall length of about 35 cm, although other dimensions are contemplated depending upon the targeted anatomy. Proximal portion 200a of periscope 200 is configured for attachment to the viewing portion of an endoscope or visualization catheter by way of an attachment means, such as elastic friction fit 104. Other means for attachment are contemplated including, but not limited to, an adhesive, a clamp, a snap-fit connection, a threaded connection, a magnetic connection, a vacuum connection, or combination thereof.

Disposed within periscope 200 is light fiber 108 that is concentric with light source 116 of endoscope 102. Accordingly, light fiber 108 of periscope 200 extends the reach of light from endoscope 102. Light fiber 108 is preferably about 35 cm long, although other dimensions are contemplated.

Also disposed within periscope 200 is lens stack 118. Lens stack 118 is disposed at proximal portion 200a of periscope 200 and between camera lens 112 of endoscope 102 and camera optical fiber 110 of periscope 200. Camera optical fiber 110 is preferably a single fiber optic cable that is about 15-20 cm long and is concentric with camera lens 112 of endoscope 102. There between the proximal end of camera optical fiber 110 and camera lens 112 of endoscope 102 is lens stack 118 that provides for focusing of the image targeted at distal end 200b of periscope 200. Accordingly, an image is viewed at distal end 200b of periscope 200 with camera optical fiber 110 and brought into focus with lens stack 118 and viewed by camera lens 112 of endoscope 102. Alternatively, one or more additional lens stacks may be placed at distal end 200b, elsewhere, or external to periscope 200 to further enhance or alter the focus of the target site. Camera optical fiber 110, lens stack 118, and light fiber 108 are coupled to the distal end of endoscope 102 to prevent misalignment during use.

Because light source 116 of endoscope 102 and the targeted image site are spaced a set distance apart at its distal end, light fiber 108 and camera optical fiber 110 may have a transition length along body 222, such as tapered portion 220. Tapered portion 220 may extend any distance between and including proximal portion 200a and distal portion 200b of periscope 100 such that light fiber 108 and camera optical fiber 110 are brought extremely close together to reduce the overall outer diameter of periscope 200. Because periscope 200 does not include an accessory channel, the outer diameter at distal portion 200b of periscope is able to be minimized. However, distal portion 200b of periscope 200 still includes enough open space so that a wire-guide may pass therethrough to provide a means for directing periscope 200 to the target anatomy.

Body 222 of periscope 200 may be made from numerous materials such that it is configured with sufficient flexibility yet maintains enough column strength to traverse the targeted anatomy. As illustrated in FIGS. 4-5, body 222 is a substantially cylindrical extruded tube although other means for manufacturing are included, such as those illustrated in conjunction with body 122 (illustrated in FIGS. 1-3).

Figure 7:
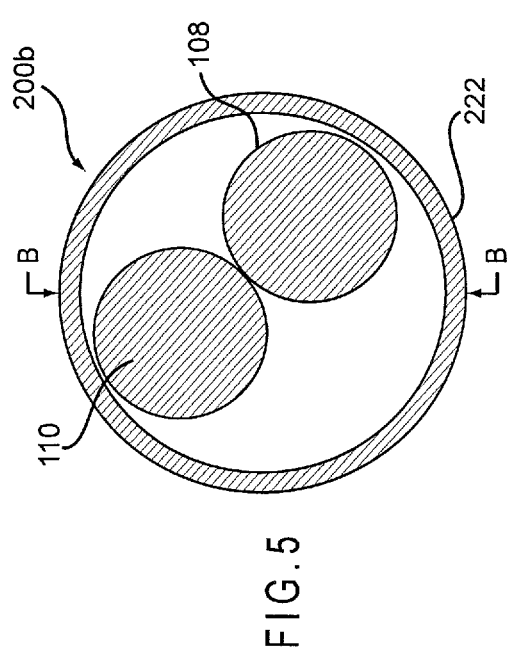
FIG. 7 illustrates a front-view at the line C-C of the periscope illustrated in FIG. 6.
Figure 6:
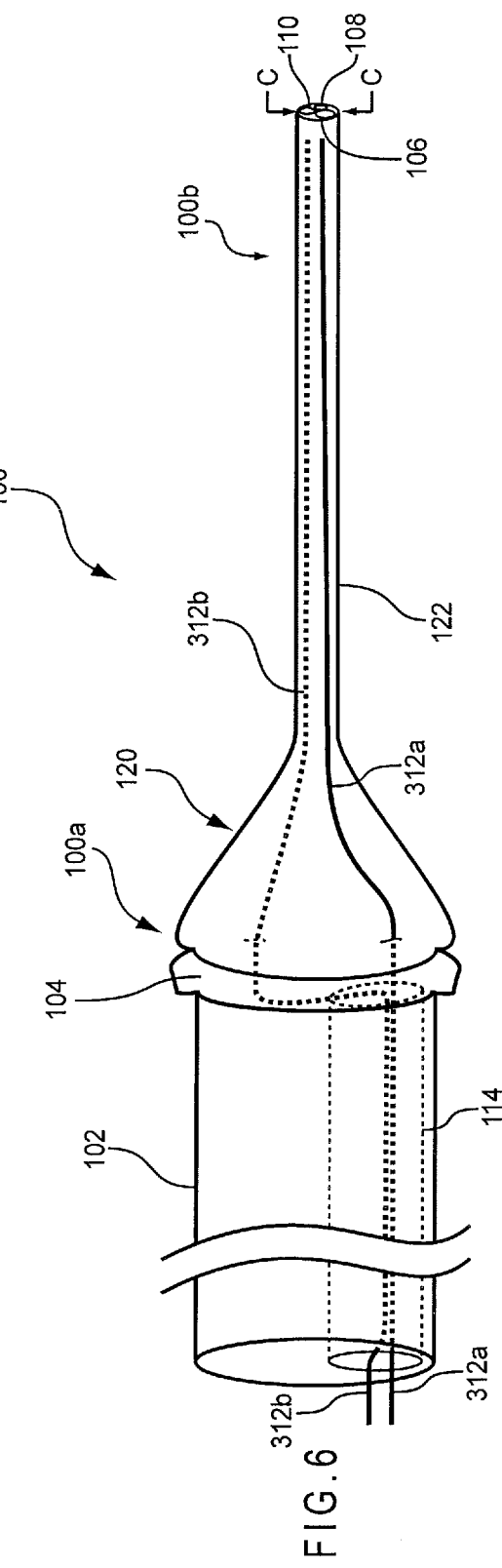
FIG. 6 illustrates a perspective view of an alternate embodiment of a periscope coupled to the viewing end of an endoscope.

FIG. 6 illustrates a perspective view of periscope 300 coupled to the viewing end of endoscope 102, and FIG. 7 illustrates a front view of periscope 300 at the line C-C illustrated in FIG. 6. Periscope 300 is similar in construction to periscope 100 (illustrated in FIGS. 1-3). Periscope 300 includes proximal portion 300a, distal portion 300b, body 322, and taper 120. Proximal portion 300a of periscope 300 is configured for attachment to the viewing portion of an endoscope or visualization catheter by way of an attachment means, such as elastic friction fit 104. Other means for attachment are contemplated including, but not limited to, an adhesive, a clamp, a snap-fit connection, a threaded connection, a magnetic connection, a vacuum connection, or combination thereof. Similar to periscope 100 (illustrated in FIGS. 1-3), disposed within periscope 300 is light fiber 108, camera optical fiber 110, lens stack (not shown), and accessory channel 106.

Periscope 300 is equipped with steering means, such as two-way steering wires 312a and 312b. Steering wires 312a and 312b are configured to attach linearly to either side of the exterior portion of body 322 such that they provide a means for two-way deflection of periscope 300. Proximal portions of steering wires 312a and 312b enter body 322 and travel through working channel 114 of endoscope 102 and exit at a proximal portion of endoscope 102. Accordingly, periscope 300 may be deflected by pulling and/or pushing either of steering wires 312a and 312b.

Alternative steering means are contemplated, including the use of one or more steering wires; one or more steering wires disposed within the luminal wall of body 322; one or more steering wires housed within an attachment that extends externally along the endoscope; and one or more steering wires surrounded by a coating on the exterior wall surface of body 322. Coatings contemplated include, but are not limited to, polytetrafluoroethylene (PTFE) or other materials having low coefficients of friction. Additional steering means are contemplated, including but not limited to, configuring a periscope (such as those illustrated herein and equivalents thereto) with other drive wires and/or pneumatic controls used alone or in combination with other steering means.

Figure 8:
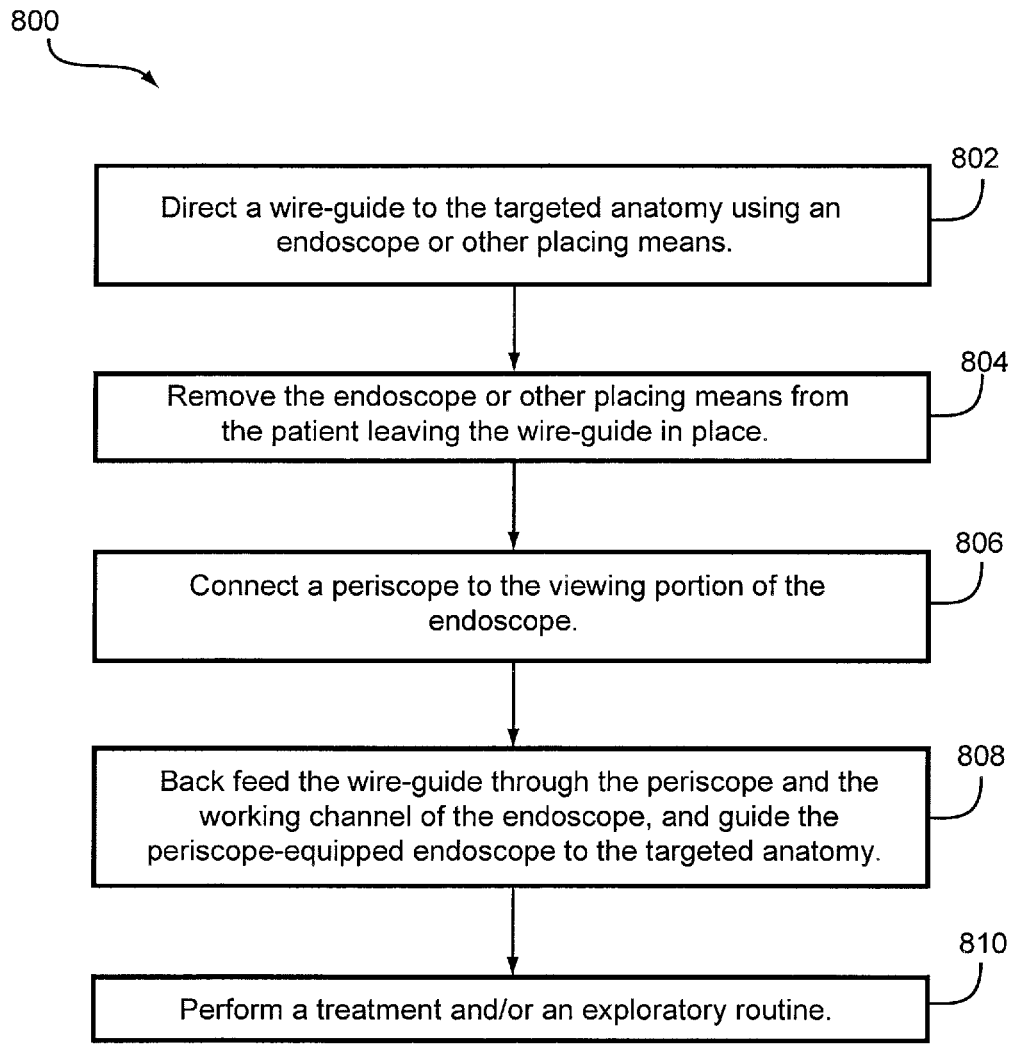
FIG. 8 illustrates a method of using a periscope, such as those illustrated herein and equivalents thereto.

FIG. 8 illustrates a method of using a periscope device, such as those illustrated herein and equivalents thereto. At block 802, using an endoscope or other placing means, a wire-guide is directed to the targeted anatomy, for example, the bile duct. At block 804, the endoscope or other placing means is removed from the patient leaving the wire-guide in place. At block 806, a periscope (such as those illustrated in FIGS. 1-7 and equivalents thereto) is connected to the viewing portion of the endoscope. At block 808, the wire-guide is back fed through the periscope and the working channel of the endoscope, guiding the periscope-equipped endoscope to the targeted anatomy, such a bile duct for direct visualization. At block 810, a treatment and/or an exploratory routine is performed.

From the foregoing, the discovery of methods and apparatuses of periscopes for use with visualization catheters and endoscopes provide numerous benefits to the medical field. It can be seen that the embodiments illustrated and equivalents thereto as well as the methods of manufacturer may utilize machines or other resources, such as human beings, thereby reducing the time, labor, and resources required to manufacturer the embodiments. Indeed, the discovery is not limited to the embodiments illustrated herein, and the principles and methods illustrated herein may be applied and configured to any visualization catheter, endoscope, and equivalents.

Those of skill in the art will appreciate that embodiments not expressly illustrated herein may be practiced within the scope of the present discovery, including that features illustrated herein for different embodiments may be combined with each other and/or with currently-known or future-developed technologies while remaining within the scope of the claims presented here. It is therefore intended that the foregoing detailed description be regarded as illustrative rather than limiting. It is understood that the following claims, including all equivalents, are intended to define the spirit and scope of this discovery. Furthermore, the advantages illustrated above are not necessarily the only advantages of the discovery, and it is not necessarily expected that all of the illustrated advantages will be achieved with every embodiment of the discovery.

What is claimed is:

1. A periscope comprising: a cylindrical body comprising a proximal portion and a distal portion; wherein proximal portion of the cylindrical body is tapered and the distal portion comprises a constant outer diameter; a first fiber optic cable disposed within the cylindrical body and extending from the proximal portion of the cylindrical body to the distal portion of the cylindrical body; a lens stack disposed within the proximal portion of the cylindrical body; and a second fiber optic cable in communication with the lens stack and extending distally therefrom, wherein the second fiber optic cable is disposed within the cylindrical body and extends to the distal portion of the cylindrical body, wherein the first fiber optic cable and the second fiber optic cable are arranged within the cylindrical body in a side-by-side fashion, and wherein the proximal portion of the cylindrical body is configured for attachment to a distal viewing end of a shaft of an endoscope such that the first fiber optic cable is coaxial with a light of the endoscope and the lens stack is coaxial with a camera of the endoscope.

2. The periscope of claim 1, wherein the endoscope comprises at least one of a forward-viewing endoscope, a side-viewing endoscope, or visualization catheter.

3. The periscope of claim 1, further comprising an accessory channel comprising a lumen disposed within the cylindrical body and extending from the proximal portion of the cylindrical body through the distal portion of the cylindrical body.

4. The periscope of claim 3, wherein the accessory channel is coaxial with a working channel of the endoscope.

5. The periscope of claim 1, wherein the proximal portion of the cylindrical body further comprises an attachment means for attachment to a viewing end of an endoscope.

6. The periscope of claim 5, wherein the attachment means comprises at least one of an elastic friction fit, an adhesive, a clamp, a snap-fit connection, a threaded connection, a magnetic connection, or a vacuum connection.

7. The periscope of claim 1, further comprising a deflection wire in communication with the distal portion of the cylindrical body and configured to deflect the distal portion of the cylindrical body.

8. The periscope of claim 7, wherein the deflection wire is attached linearly to the proximal portion and the distal portion of the cylindrical body.

9. A periscope comprising: a cylindrical body comprising a proximal portion and a distal portion; wherein proximal portion of the cylindrical body is tapered and the distal portion comprises a constant outer diameter; a first fiber optic cable disposed within the cylindrical body and extending from the proximal portion of the cylindrical body to the distal portion of the cylindrical body; a lens stack disposed at within the proximal portion of the cylindrical body; a second fiber optic cable in communication with the lens stack and extending distally therefrom, wherein the second fiber optic cable is disposed within the cylindrical body and extends to the distal portion of the cylindrical body; and an accessory channel comprising a lumen disposed within the cylindrical body and extending from the proximal portion of the cylindrical body through the distal portion of the cylindrical body; wherein the first fiber optic cable, the second fiber optic cable and the accessory channel are arranged within the cylindrical body in a side-by-side fashion, and wherein the proximal portion of the cylindrical body further comprises an attachment means configured for attachment to a distal viewing end of a shaft of an endoscope such that the first fiber optic cable is coaxial with a light of the endoscope, the lens stack is coaxial with a camera of the endoscope, and the accessory channel is coaxial with a working channel of the endoscope.

10. The periscope of claim 9, wherein the endoscope comprises at least one of a forward-viewing endoscope, a side-viewing endoscope, or visualization catheter.

11. The periscope of claim 9, wherein the attachment means comprises at least one of an elastic friction fit, an adhesive, a clamp, a snap-fit connection, a threaded connection, a magnetic connection, or a vacuum connection.

12. The periscope of claim 9, further comprising a deflection wire in communication with the distal portion of the cylindrical body and configured to deflect the distal portion of the cylindrical body.

13. The periscope of claim 12, wherein the deflection wire is attached linearly to the proximal portion and the distal portion of the cylindrical body.

14. A method of using a periscope device comprising: directing a wire-guide to a target site; connecting a periscope to a distal viewing end of a shaft of an endoscope; wherein the periscope is configured to extend the view of the endoscope; back-feeding the wire-guide through the periscope and a working channel of the endoscope; and guiding the periscope to the target site; wherein the periscope comprises: a cylindrical body comprising a proximal portion and a distal portion; wherein the cylindrical body is tapered along at least a portion of the cylindrical body; a first fiber optic cable disposed within the cylindrical body and extending from the proximal portion of the cylindrical body to the distal portion of the cylindrical body; a lens stack in communication with the cylindrical body; and a second fiber optic cable in communication with the lens stack, wherein the second fiber optic cable is disposed within the cylindrical body and extends to the distal portion of the cylindrical body; and wherein the proximal portion of the cylindrical body further comprises an attachment means configured for attachment to a distal viewing end of a shaft of an endoscope such that the first fiber optic cable is coaxial with a light of the endoscope and the lens stack is coaxial with a camera of the endoscope.

15. The method of claim 14, wherein the periscope further comprises an accessory channel comprising a lumen disposed within the cylindrical body and extending from the proximal portion of the cylindrical body through the distal portion of the cylindrical body, wherein the accessory channel is to be coaxial with a working channel of the endoscope.

16. The method 14, further comprising performing at least one of a treatment or exploratory routine using the periscope.

17. The method of claim 14, wherein the directing a wire-guide to a target site further comprises using an endoscope to direct the wire-guide to the target site.

18. The method of claim 14, wherein the endoscope comprises at least one of a forward-viewing endoscope, a side-viewing endoscope, or visualization catheter.

\* \* \* \* \*

UNITED STATES PATENT AND TRADEMARK OFFICE
CERTIFICATE OF CORRECTION

PATENT NO. : 9,119,531 B2  
APPLICATION NO. : 13/659001  
DATED : September 1, 2015  
INVENTOR(S) : Vihar C. Surti et al.

Page 1 of 1

It is certified that error appears in the above-identified patent and that said Letters Patent is hereby corrected as shown below:

<u>In the Claims</u>

In column 8, claim 9, line 28, after "a lens stack disposed" delete "at".

Signed and Sealed this
Twenty-fourth Day of May, 2016

Michelle K. Lee
*Director of the United States Patent and Trademark Office*